「12」 United States Patent
Bovenkamp et al.

(10) Patent No.: US 9,204,947 B2
(45) Date of Patent: Dec. 8, 2015

(54) SYSTEM FOR DETERMINING AMPLITUDE OF A POWER TOOTHBRUSH BRUSHHEAD IN THE MOUTH

(71) Applicant: KONINKLIJKE PHILIPS N.V., Eindhoven (NL)

(72) Inventors: Marc Darrin Bovenkamp, Snoqualmie, WA (US); Scott E Hall, Issaquah, WA (US); Jeffrey Michael Alexander, North Bend, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1 day.

(21) Appl. No.: 14/353,246

(22) PCT Filed: Oct. 17, 2012

(86) PCT No.: PCT/IB2012/055656
§ 371 (c)(1),
(2) Date: Apr. 21, 2014

(87) PCT Pub. No.: WO2013/061214
PCT Pub. Date: May 2, 2013

(65) Prior Publication Data
US 2014/0259472 A1    Sep. 18, 2014

Related U.S. Application Data

(60) Provisional application No. 61/550,602, filed on Oct. 24, 2011.

(51) Int. Cl.
A61C 17/34    (2006.01)
A61C 17/22    (2006.01)
A61C 17/32    (2006.01)

(52) U.S. Cl.
CPC ............... *A61C 17/221* (2013.01); *A61C 17/34* (2013.01); *A61C 17/32* (2013.01)

(58) Field of Classification Search
CPC ...... A61C 17/22; A61C 17/221; A61C 17/32; A61C 17/34; A61C 17/3409; A46B 13/02; A46B 2200/1066
See application file for complete search history.

(56) References Cited

U.S. PATENT DOCUMENTS

| | | | |
|---|---|---|---|
| 8,690,579 B2 * | 4/2014 | Ikkink et al. | 434/263 |
| 2011/0010875 A1 | 1/2011 | Iwahori et al. | |
| 2011/0010876 A1 | 1/2011 | Iwahori et al. | |
| 2011/0041269 A1 | 2/2011 | Iwahori | |
| 2013/0000670 A1 * | 1/2013 | Binner et al. | 134/6 |

* cited by examiner

*Primary Examiner* — Laura C Guidotti

(57) ABSTRACT

The power toothbrush includes a handle (12), a brushhead (14) and a drive assembly (20) which includes a processor (22) for driving the brushhead at a selected frequency and amplitude. A miniature gyroscope (MEMS) (26) and an accelerometer (28) are mounted on the brushhead or on a portion of the drive assembly within the handle for detecting rotational velocity of the brushhead and orientation of the brushhead in the mouth during operation. Information from the gyroscope (rotational) and the accelerometer are then provided to the processor for determining amplitude of brushhead movement. The amplitude information is provided to the user, or can be further processed and fed back (30) to the drive assembly for control of brushhead movement.

11 Claims, 3 Drawing Sheets

SYSTEM FOR DETERMINING AMPLITUDE OF A POWER TOOTHBRUSH BRUSHHEAD IN THE MOUTH

CROSS-REFERENCE TO PRIOR APPLICATIONS

This application is the U.S. National Phase application under 35 U.S.C. §371 of International Application No. PCT/IB2012/055656, filed on Oct. 17, 2012, which claims the benefit of U.S. Provisional Patent Application No. 61/550,602, filed on Oct. 24, 2011. These applications are hereby incorporated by reference herein.

This invention relates generally to power toothbrushes, and more specifically concerns the determination of rotational amplitude and/or other motion of a power toothbrush brushhead when the power toothbrush is operating within the mouth.

In the operation of a power toothbrush, it is important to determine the on-going performance of the toothbrush, i.e. the effectiveness of the brushing action. One way to maintain effectiveness is to maintain the desired pre-set frequency of operation of the toothbrush. This is done routinely in power toothbrushes, particularly resonant drive power toothbrushes, by action of the processor present in the toothbrush, typically in the handle portion thereof.

Another way to determine operational effectiveness is to determine the amplitude of movement of the brushhead. This is often done during testing following manufacture of the toothbrush by an in vitro process/arrangement, i.e. when the toothbrush is outside the mouth, using various known systems to measure both amplitude and frequency. However, such an in vitro system cannot be used for in vivo (in the mouth) determinations. A rotary encoder-based measurement system can be used, positioned near the handle coupling end of the brushhead. However, such a system does not take the brush neck structure into consideration and does not determine or measure displacement. There is no known effective structure/method for direct amplitude determination of the brushhead during actual/normal operation of the toothbrush in the mouth.

Accordingly, it is desirable for a power toothbrush to have an in vivo brushhead amplitude determination capability.

Accordingly, such a power toothbrush comprises: a handle; a brushhead; a drive assembly, including a processor, for driving the brushhead at a selected frequency and amplitude, the drive assembly being located within the handle; a miniature gyroscope mounted on the brushhead or on a portion of the drive assembly within the handle for detecting rotational velocity of the brushhead when the brushhead is operating in the mouth of a user; and wherein the processor is capable of processing the rotational velocity information from the gyroscope to provide amplitude information of brushhead movement, wherein said amplitude information is provided to the user or used to control brushhead operation.

Figure 1:
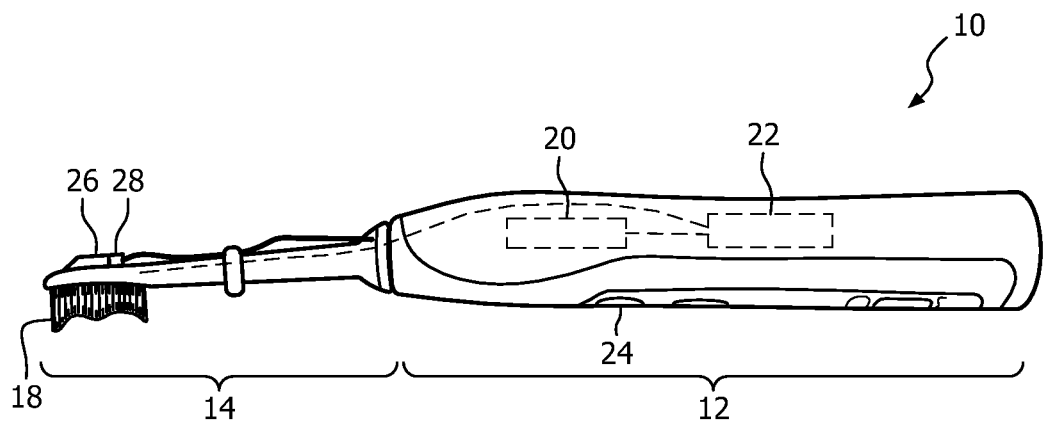
FIG. 1 shows a simplified schematic view of a power toothbrush showing an in vivo amplitude determination system.
Figure 2:
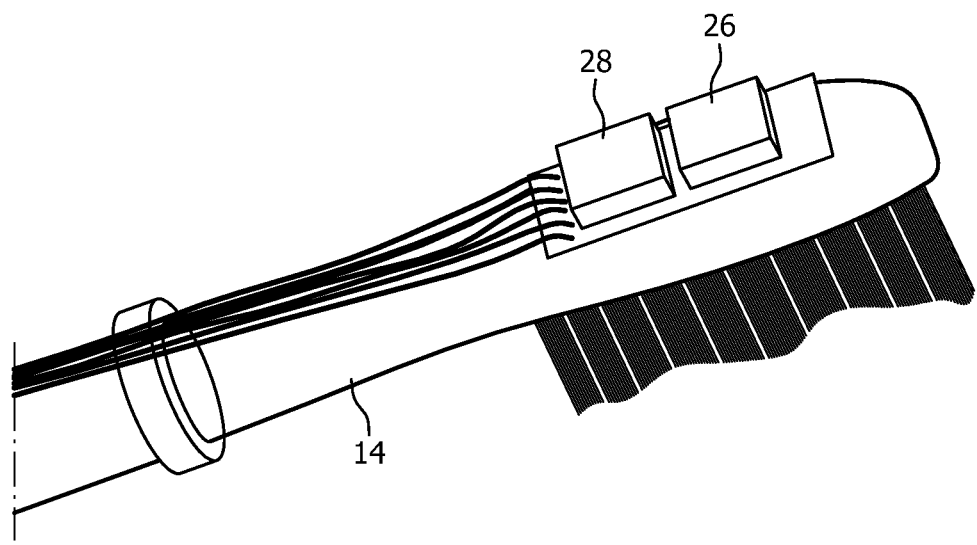
FIG. 2 is a close-up view of a portion of the structure of FIG. 1.

FIGS. 1 and 2 show a simplified view of the amplitude determination system disclosed herein. FIG. 1 shows a power toothbrush 10 having a handle portion 12 and a removable brushhead portion 14 with a bristle field section 18 at the distal end thereof. Internally of the handle is a drive/power system 20 for the brushhead and a processor 22 for controlling the action of the drive/power system. Drive/power system 20 and processor 22 are generally conventional and well-known in the art of power toothbrushes. The toothbrush 10 is controlled by an on/off switch 24 and may include other conventional operation capability, including various modes of operation, controlled by processor 22.

In the embodiment of FIGS. 1 and 2, a MEMS (micro-electro-mechanical-system) gyroscope 26, such as manufactured by ST Microelectronics, and an accelerometer 28 are positioned on the brushhead 14 at the rear of the bristle field. Power is provided to the gyroscope 26 and the accelerometer 28 by drive/power system 20. Velocity data obtained during operation of the toothbrush is transmitted back through wires or other communication elements to the control processor. While gyroscope 26 and accelerometer 28 and connecting power/data lines 30 are visible in FIGS. 1 and 2, in a commercial toothbrush, they will typically be concealed. Line connections in a selected form are provided between brushhead 14 and the handle 12 to permit convenient removal and insertion of brushheads thereto. As indicated above, gyroscope 26 typically is a MEMS gyroscope such as manufactured by ST Microelectronics. MEMS gyroscopes are well-known commercial devices which use a pendulum vibrating element to measure rotational velocity of the brushhead as it moves. Presently available MEMs gyroscopes have the necessary amplitude measurement capability, with 6K degrees per second (dps) components. Higher values of dps components would increase performance of the system.

The rotational velocity information is provided to the control processor 22, which by a routine calculation converts the velocity information to an amplitude number. This is well-known in the art, using the known frequency of brushhead oscillation. A typical frequency for a resonant power toothbrush is 230-290 Hz, although this can be varied.

The processor 22 filters out user-imparted motion and other undesirable signals and determines the amplitude of motion, either peak or peak-to-peak thereof. With such a power toothbrush, to have effective brushing, peak-to-peak amplitude is typically within the range of 9-11°, with 10° being optimal, although again this value can be varied, depending upon the particular toothbrush.

Figure 5:
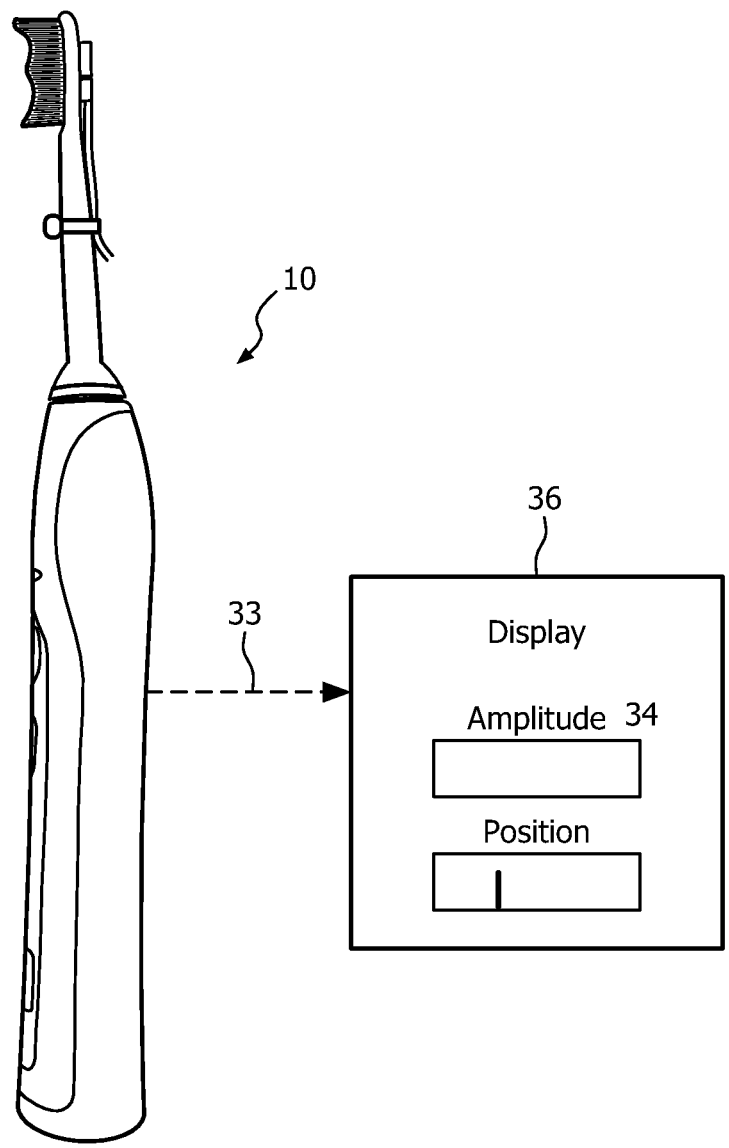
FIG. 5 is a simplified representation of a system in which brushhead amplitude information is provided to a base unit separate from the power toothbrush.

The amplitude information determined by the processor can then be compared at 31 with a desired amplitude range and an output provided, indicating that the amplitude is within the desired range or outside thereof. Alternatively, or in addition, the amplitude information can be provided to the user, either by an auditory or visual representation, represented at 34 generally, either on the toothbrush itself or through a communications link 33 to a base unit 36 (FIG. 5). Information can also be provided concerning the position of the brushhead relative to selected regions of the teeth. The communication to the base typically is RF communication. The user can use that information to change his/her brushing habits, such as decreasing the pressure of the bristles against the teeth, which could affect the amplitude of the brushhead. In this way, the user obtains direct information relative to the possible effectiveness (or ineffectiveness) of the brushing and his/her use of the toothbrush.

Figure 3:
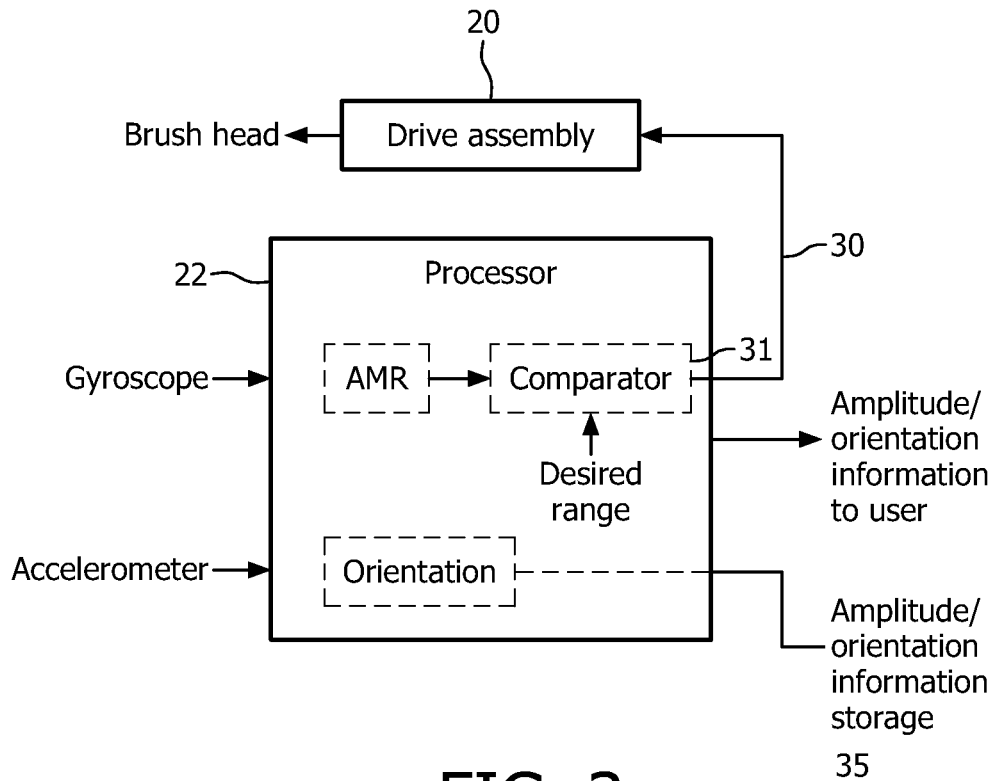
FIG. 3 is a simplified feedback/control system for the power toothbrush using amplitude information.

Alternatively, referring to FIG. 3, the information from the processor can be used through a feedback line 30 to the drive assembly to change an aspect of the drive signal, such as the frequency of the drive signal or the duty cycle of the drive signal to change the amplitude back to the desired value. This arrangement is useful when the user is generally brushing correctly, but due to other factors, such as a reduction in battery power, the brush effectiveness is below a desired value.

The purpose of the present system is to use in vivo brushhead amplitude information during actual brushing operation as a measurement of effective brushing. Amplitude information can be used by the system itself to maintain/improve the effectiveness of the brushing by maintaining the brushhead amplitude within a known desired range.

As indicated above, a MEMS gyroscope is used to obtain rotational velocity, which can be used to determine rotational amplitude. Rotational velocity can also be obtained by an accelerometer, although there are limitations. The gyroscope is immune to non-rotational forces.

The system can also include an accelerometer 28 (FIG. 2) with the gyroscope. The accelerometer can be used to determine a change of position of the brushhead in the mouth (apart from rotational movements), so that amplitude can be correlated with selected regions of the mouth. The combination of the MEMS gyrometer and the accelerometer enables the system to determine both rotational and translational motion. The combination of accelerometer information and the MEMS gyroscope information (after processing) provides information concerning the effectiveness of the brushing over the entire oral region. It should be understood, however, that the MEMS gyroscope alone provides the desired information with respect to amplitude determination (after processing). The same is true for the accelerometer alone, with some limitations.

Figure 4:
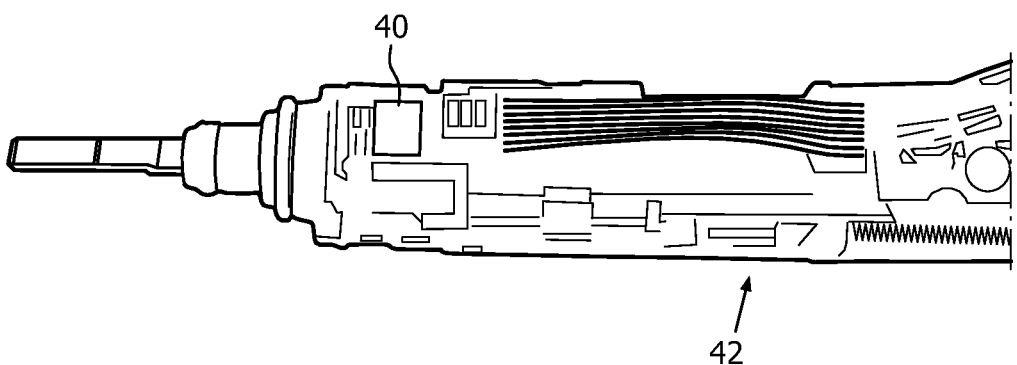
FIG. 4 is a simplified schematic view of an alternative embodiment of the brushhead amplitude determination system.

FIGS. 1 and 2 show the gyroscope and the accelerometer positioned on the brushhead, typically at the base of the bristle field. However, the gyroscope and/or the accelerometer can be positioned on other locations on the brushhead and also can be positioned within the handle. FIG. 4 shows an arrangement where the gyroscope and accelerometer are positioned on a "hub" portion of the drive system, i.e. a portion of the drive system, such as a base portion of the driveshaft 40 in the handle 42 which connects with the brushhead. In this arrangement, there is no requirement for data or power lines between the brushhead and the handle portions, since all the elements are within the handle. Alternatively, one element, e.g. the gyroscope, could be on the brushhead and the other, e.g. the accelerometer in the handle or vice versa.

Accordingly, a system has been disclosed which uses a miniature gyroscope (MEMS) to measure angular velocity of a power toothbrush brushhead, from which amplitude of the brushhead movement can be determined. An accelerometer could also be used, although with limitations, since it is subject to non-rotational forces. The system is capable of measuring angular velocity in vivo, i.e. within the mouth, when the toothbrush is operating. Amplitude information is important relative to the effectiveness of the brushing.

The information obtained can also be stored for later analysis. The storage system, represented generally at 35 in FIG. 3, can be in the handle, the brushhead or the base unit.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. A power toothbrush, comprising:
  a handle;
  a drive assembly, including a processor, for driving a brushhead at a selected frequency of brushhead oscillation and amplitude of brushhead motion, the drive assembly being located within the handle;
  an accelerometer which provides information as to an orientation of the brushhead in the user's mouth and
  a miniature gyroscope for detecting angular velocity of a brushhead motion, when the brushhead is operating in a user's mouth,
  wherein one of the gyroscope and the accelerometer is located in (i) the brushhead and the other is located (ii) in the handle
  wherein the processor is configured for processing angular velocity information from the gyroscope to provide amplitude information of the brushhead motion, and wherein said amplitude information of the brushhead motion is at least one selected from the group consisting of (i) provided to the user and (ii) used to control brushhead operation.

2. The toothbrush of claim 1, wherein the amplitude information of the brushhead motion is provided both to the user and used to control brushhead operation.

3. The toothbrush of claim 1, wherein the amplitude information of the brushhead motion provided to the user is at least one selected from the group consisting of audible and visible to the user.

4. The toothbrush of claim 1, further comprising a storage system for storing the amplitude information of the brushhead motion for later analysis.

5. The toothbrush of claim 1, further comprising a comparison circuit for comparing the amplitude information of the brushhead motion with a pre-established range of values, and if the amplitude information of the brushhead motion is outside of said pre-established range of values, a feedback control signal is provided to the drive assembly to change a characteristic of a drive signal used to control brushhead operation in order to alter the amplitude of brushhead motion to a selected range.

6. The toothbrush of claim 5, wherein the characteristic is a frequency of the drive signal or a duty cycle of the drive signal.

7. The toothbrush of claim 1, wherein the amplitude information of the brushhead motion is peak-to-peak amplitude of brushhead motion.

8. The toothbrush of claim 1, wherein the amplitude information of the brushhead motion is peak amplitude of brushhead motion.

9. The toothbrush of claim 1, further comprising a base display unit separate from the toothbrush (i) for displaying the amplitude information of the brushhead motion and (ii) for implementing a communication capability between the toothbrush and the base display unit.

10. A power toothbrush, comprising:
  a handle;
  a brushhead;
  a drive assembly, including a processor, for driving a brushhead at a selected frequency of brushhead oscillation and amplitude of brushhead motion, the drive assembly being located within the handle; and
  an accelerometer mounted on the brushhead or on a portion of the drive assembly within the handle, the accelerometer for detecting forces present on the accelerometer due to motion of the brushhead, including an angular velocity of the brushhead motion, when the brushhead is operating in a user's mouth,
  wherein the processor is capable of processing angular velocity information from the accelerometer to provide amplitude information of the brushhead motion, wherein said amplitude information of the brushhead motion is provided to the user and used to control brushhead operation.

11. The toothbrush of claim 10, further comprising a comparison circuit for comparing the amplitude information of the brushhead motion with a pre-established range of values, and if the amplitude information of the brushhead motion is outside of said pre-established range of values, a feedback control signal is provided to the drive assembly to change a characteristic of a drive signal used to control brushhead operation in order to alter the amplitude of brushhead motion to a selected range.

* * * * *